(12) United States Patent
Cohen

(10) Patent No.: US 9,445,745 B2
(45) Date of Patent: Sep. 20, 2016

(54) TOOL SHAPE ESTIMATION

(75) Inventor: Amit Cohen, Binyamina (IL)

(73) Assignee: MediGuide Ltd., Haifa (IL)

( * ) Notice: Subject to any disclaimer, the term of this patent is extended or adjusted under 35 U.S.C. 154(b) by 807 days.

(21) Appl. No.: 12/906,420

(22) Filed: Oct. 18, 2010

(65) Prior Publication Data

US 2011/0160571 A1 Jun. 30, 2011

Related U.S. Application Data

(60) Provisional application No. 61/291,478, filed on Dec. 31, 2009.

(51) Int. Cl.
*A61B 5/00* (2006.01)
*A61B 5/06* (2006.01)
*A61B 8/08* (2006.01)

(52) U.S. Cl.
CPC .................. *A61B 5/06* (2013.01); *A61B 5/066* (2013.01); *A61B 8/0833* (2013.01); *A61B 8/5238* (2013.01); *A61B 5/7289* (2013.01); *A61B 34/20* (2016.02)

(58) Field of Classification Search
CPC .............................. A61B 5/066; A61B 8/5238
USPC ........................................................ 600/424
See application file for complete search history.

(56) References Cited

U.S. PATENT DOCUMENTS

| | | | |
|---|---|---|---|
| 5,603,318 A | 2/1997 | Heilbrun et al. | |
| 6,233,476 B1 | 5/2001 | Strommer et al. | |
| 6,498,944 B1 | 12/2002 | Ben-Haim et al. | |
| 6,788,967 B2 | 9/2004 | Ben-Haim et al. | |
| 6,920,347 B2 | 7/2005 | Simon et al. | |
| 7,197,354 B2 | 3/2007 | Sobe | |
| 7,263,397 B2 | 8/2007 | Hauck et al. | |
| 7,343,195 B2 | 3/2008 | Strommer et al. | |
| 7,386,339 B2 | 6/2008 | Strommer et al. | |
| 2004/0006268 A1 | 1/2004 | Gilboa et al. | |
| 2004/0254437 A1 | 12/2004 | Hauck et al. | |
| 2005/0107688 A1 | 5/2005 | Strommer | |

(Continued)

FOREIGN PATENT DOCUMENTS

EP 1862114 12/2007

OTHER PUBLICATIONS

International Search Report and Written Opinion for PCT/US2010/054720 mailed Dec. 22, 2010.

(Continued)

*Primary Examiner* — Jonathan Cwern
(74) *Attorney, Agent, or Firm* — Dykema Gossett PLLC

(57) ABSTRACT

A medical tool includes a location sensor at a distal end. While the tool is being maneuvered to a desired region of interest, a control unit records a first location reading obtained according to an output from the sensor when requested by a user, indicative of when a patient's anatomy constrains free movement of the tool in at least one degree of freedom. Once the tool has reached the region of interest, the control unit records a second location reading according to the sensor output indicative of a current location. A relaxation shape of the tool forms a shape constraint on the tool shape reconstruction. The control unit determines a reconstruction representing the current shape of the tool based on the positional constraints and the shape constraint. The reconstruction is graphically superimposed on an image of the region of interest.

19 Claims, 6 Drawing Sheets

(56) References Cited

U.S. PATENT DOCUMENTS

| | | |
|---|---|---|
| 2006/0004286 A1 | 1/2006 | Chang et al. |
| 2006/0036167 A1* | 2/2006 | Shina .......................... 600/433 |
| 2006/0058647 A1 | 3/2006 | Strommer et al. |
| 2008/0200794 A1 | 8/2008 | Teichman et al. |
| 2009/0137952 A1 | 5/2009 | Ramamurthy et al. |

OTHER PUBLICATIONS

Supplementary European Search Report from EP Application No. 10841432.7 (Oct. 10, 2014).

* cited by examiner

TOOL SHAPE ESTIMATION

CROSS-REFERENCE TO RELATED APPLICATIONS

This application claims the benefit of U.S. Provisional application Ser. No. 61/291,478 filed 31 Dec. 2009 entitled TOOL SHAPE ESTIMATION, the entire disclosure of which is hereby incorporated by reference herein.

BACKGROUND OF THE INVENTION a. Field of the Invention

The instant invention relates generally to medical imaging and more particularly to a system and method for tool shape estimation.

b. Background Art

When a medical tool (e.g., a catheter) is inserted into a patient and navigated to a region of interest, a clinician using the tool may require specific knowledge of the shape of the tool within the region of interest. Conventional approaches for determining the shape typically involve extensive use of fluoroscopy (i.e., a manual determination of the shape of the tool). It would be desirable to reduce or eliminate the use of fluoroscopy in order to reduce patient exposure to x-rays.

An approach taken in the art for estimating tool shape involves providing a system for detecting (during use) the location of a position sensor embedded in a catheter and then rendering the catheter tip based on the detected sensor location, as seen by reference to U.S. Pat. No. 6,233,476 entitled MEDICAL POSITIONING SYSTEM to Strommer et al., hereby incorporated by reference in its entirety. Strommer et al. disclose rendering a representation of the tool on a display based only on the location reading from the sensor. Despite this improvement over manual tool shape estimation, there remains a desire for tool shape estimation, particularly for curved tools, within a region of interest without extensive use of fluoroscopy.

There is therefore a need for a system and method for estimating tool shape that minimizes or eliminates one or more of the problems set forth above.

BRIEF SUMMARY OF THE INVENTION

One advantage of the apparatus and methods described, depicted and claimed herein relates to the ability to accurately determine the shape of a medical tool (e.g., a catheter) within a region of interest in a patient's body (or cavity thereof) with only a reduced (i.e., minimal) use of supplemental imaging such as fluoroscopy.

This disclosure is directed to an apparatus and method for determining a shape of a medical tool. The medical tool preferably includes a location sensor disposed therein or affixed thereto (e.g., at the distal end or tip). The apparatus includes a localization system (e.g., a medical positioning system (MPS)) configured to output a location reading indicative of the sensor's location in a reference coordinate system. A control unit is configured to produce a reconstruction representing the tool's shape as a function of (1) one or more positional constraints, which may include a first location in the coordinate system defined by a point along a tool path where the patient's body anatomically constrains free movement of the tool in at least one degree of freedom and (2) a shape constraint corresponding to a relaxation shape of the tool. The positional constraint may be further defined by a second location indicative of the tool's current location (e.g., the tool's location at a time the reconstruction is performed).

The first location may be obtained by capturing an MPS location reading when the tool is observed (e.g., by a user according to an x-ray image of the region of interest) to be constrained by the body. In an embodiment, a superimposing processor is configured to superimpose the reconstruction of the tool's shape on an image of the region of interest that was acquired at an earlier time. In this regard, for superimposition, the control unit also determines the location of the tool shape reconstruction in the reference coordinate system (i.e., the MPS coordinate system). In a further embodiment, the control unit is configured to use a further location reading obtained from another location sensor disposed at a different point in the tool (e.g., a mid-tool location). The relaxation shape of the tool may be determined in accordance with a model (e.g., defined by a polynomial expression) or may alternatively be determined during use in accordance with an alternate embodiment described below.

In an alternate embodiment, the relaxation shape of the tool may be determined during use. The tool includes a guidewire disposed within a lumen formed in the tool (e.g., catheter) extending between proximal and distal ends. The guidewire has a location sensor, for example, at its distal end. The tool is first maneuvered into a stable position. The control unit then records a plurality of location readings in accordance with the output of the guidewire's location sensor while the guidewire is advanced or withdrawn through the catheter (i.e., relative movement between the stable catheter and the moving guidewire so as to accurately record the catheter's shape). The control unit is configured to then determine the tool's relaxation shape based on the recorded location readings. Through the use of information external to the measured location readings (e.g., a positional constraint indicative of an anatomical constraint, a constrictive landmark, a relaxation shape, etc.), the use of fluoroscopy in determining the shape of a medical tool can be reduced thereby also reducing the patient's exposure to x-rays.

These and other benefits, features, and capabilities are provided according to the structures, systems, and methods depicted, described and claimed herein.

DETAILED DESCRIPTION OF THE INVENTION

Figure 1:
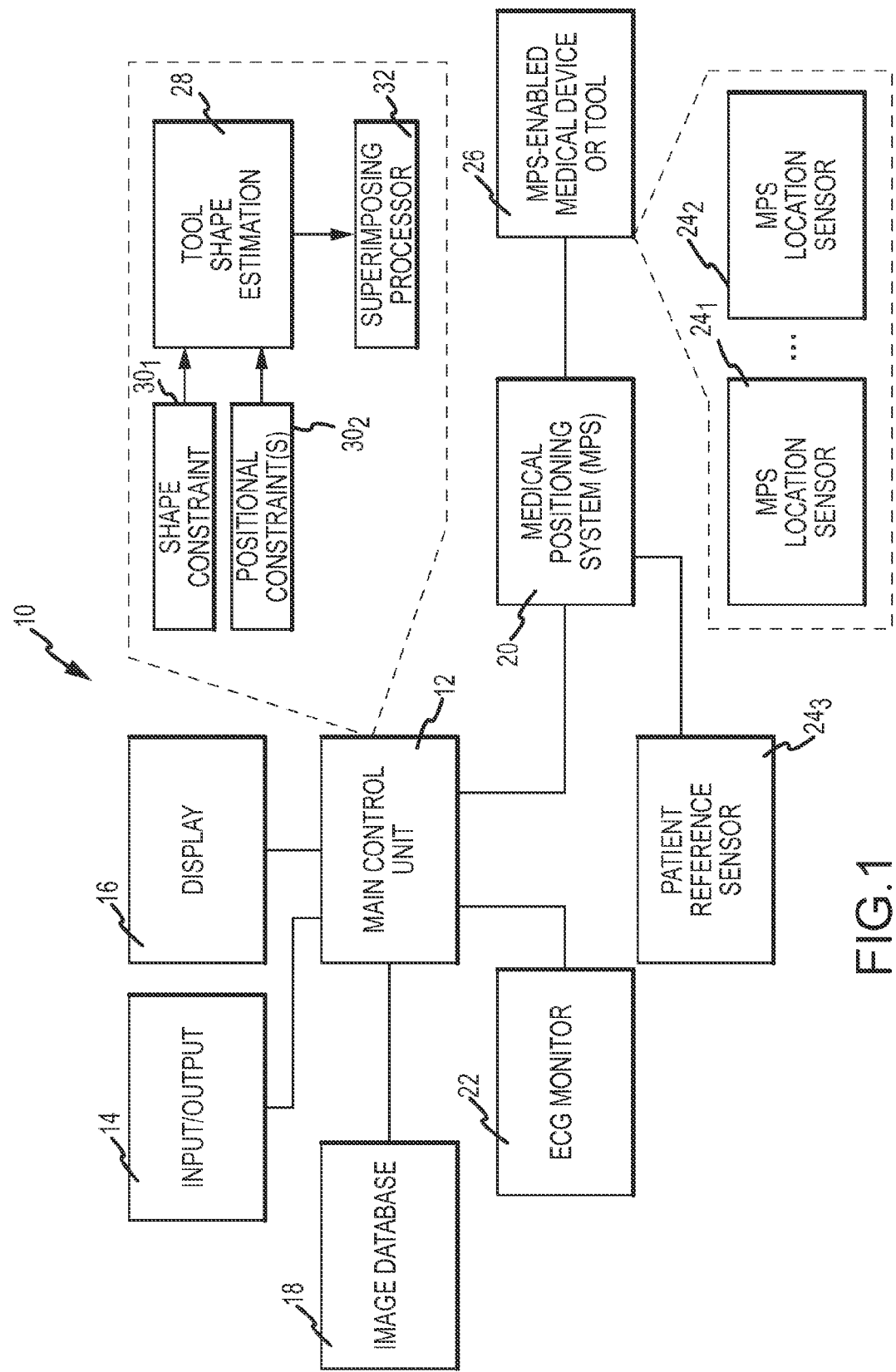
FIG. 1 is a schematic and block diagram view of a system incorporating an embodiment of a system for tool shape reconstruction.

Referring now to the drawings wherein like reference numerals are used to identify identical components in the various views, FIG. 1 is a diagrammatic view of a system 10 in which aspects of a medical tool shape reconstruction or estimation system may be embodied. It should be understood that while embodiments will be described in connection with a magnetic field-based positioning system in a catheter-lab environment, this is exemplary only and not limiting in nature.

There is a desire to reduce a patient's exposure to x-rays, such as may be used in live fluoroscopy, at least for the purpose of determining the shape (and location) of a medical tool within the patient's body. The methods and apparatus described herein reduce the need for continuous exposure or extensive use of fluoroscopy for such purposes.

With continued reference to FIG. 1, the system 10 as depicted includes a main control unit 12 (e.g., a processor) having various input/output mechanisms 14, a display 16, an optional image database 18, a localization system such as a medical positioning system (MPS) 20, an electrocardiogram (ECG) monitor 22, one or more MPS location sensors respectively designated $24_1$, $24_2$ and $24_3$, and an MPS-enabled medical device or tool 26 which itself includes one and optionally more MPS location sensors, shown in exemplary fashion as having two such sensors $24_1$ and $24_2$.

The control unit 12 is programmed to perform a plurality of functions, including a tool shape reconstruction or estimation function performed by a tool shape reconstruction or estimation block 28. In this regard, the estimation block 28 is configured to produce a reconstruction of the tool's shape as a function of (1) inputs from a shape constraint input block $30_1$, which inputs may include a relaxation shape of the tool and (2) inputs from a positional constraints input block $30_2$, which inputs may include not only the tool's current location from one or more tool location sensors but may also include one or more locations corresponding to points along the tool path where the patient's body anatomically constrains the free movement of the tool in at least one degree of freedom. The positional constraints may also include locations of other anatomically constricting landmarks and the like.

The estimation block 28, may also determine the location in a reference coordinate system of the tool shape reconstruction. The reference coordinate system may be the coordinate system of MPS 20. The tool shape reconstruction may be used for a number of purposes, such as being superimposed (graphically) on an image of the region of interest (e.g., acquired at an earlier time). The resulting composite image may then be displayed to a user on the display 16. The user may use the composite image for navigation purposes during a medical procedure. For the superimposing function, the control unit 12 is further configured to include a superimposing processor 32.

The input/output mechanisms 14 may comprise conventional apparatus for interfacing with a computer-based control unit, for example, a keyboard, a mouse, a tablet, a foot pedal, a switch or the like. The display 16 may also comprise conventional apparatus.

Embodiments consistent with the invention may find use in navigation applications that use imaging of a region of interest (as described above). Therefore the system 10 may include the image database 18. The image database 18 may be configured to store image information relating to the patient's body, for example a region of interest surrounding a destination site for the medical tool and/or multiple regions of interest along a navigation path contemplated to be traversed by the medical tool to reach the destination site. The image data in the database 18 may comprise known image types including (1) one or more two-dimensional still images acquired at respective, individual times in the past; (2) a plurality of related two-dimensional images obtained in real-time from an image acquisition device (e.g., fluoroscopic images from an x-ray imaging apparatus, such as that shown in exemplary fashion in FIG. 2) wherein the image database acts as a buffer (live fluoroscopy); and/or (3) a sequence of related two-dimensional images defining a cine-loop (CL) wherein each image in the sequence has at least an ECG timing parameter associated therewith adequate to allow playback of the sequence in accordance with acquired real-time ECG signals obtained from the ECG monitor 22. It should be understood that the foregoing are examples only and not limiting in nature. For example, the image database may also include three-dimensional image data as well. It should be further understood that the images may be acquired through any imaging modality, now known or hereafter developed, for example X-ray, ultra-sound, computerized tomography, nuclear magnetic resonance or the like.

The MPS 20 is configured to serve as the localization system and therefore to determine positioning (localization) data with respect to one or more of the MPS location sensors $24_i$ (where i=1 to n) and output a respective location reading. The location readings may each include at least one or both of a position and an orientation (P&O) relative to a reference coordinate system, which may be the coordinate system of the MPS 20. The P&O may be expressed as a position (i.e., a coordinate in three axes X, Y and Z) and orientation (i.e., an azimuth and elevation) of the magnetic field sensor in the magnetic field relative to a magnetic field generator(s) or transmitter(s). Other expressions of a P&O (e.g., other coordinates systems) are known in the art and fall within the spirit and scope of the present invention (e.g., see for example FIG. 3 and associated text of U.S. Pat. No. 7,343,195 entitled "METHOD AND APPARATUS FOR REAL TIME QUANTITATIVE THREE-DIMENSIONAL IMAGE RECONSTRUCTION OF A MOVING ORGAN AND INTRABODY NAVIGATION" to Strommer et al, incorporated by reference in its entirety, viz. location [X, Y, Z] and orientation (angles $\alpha$, $\beta$, and $\chi$)).

Figure 2:
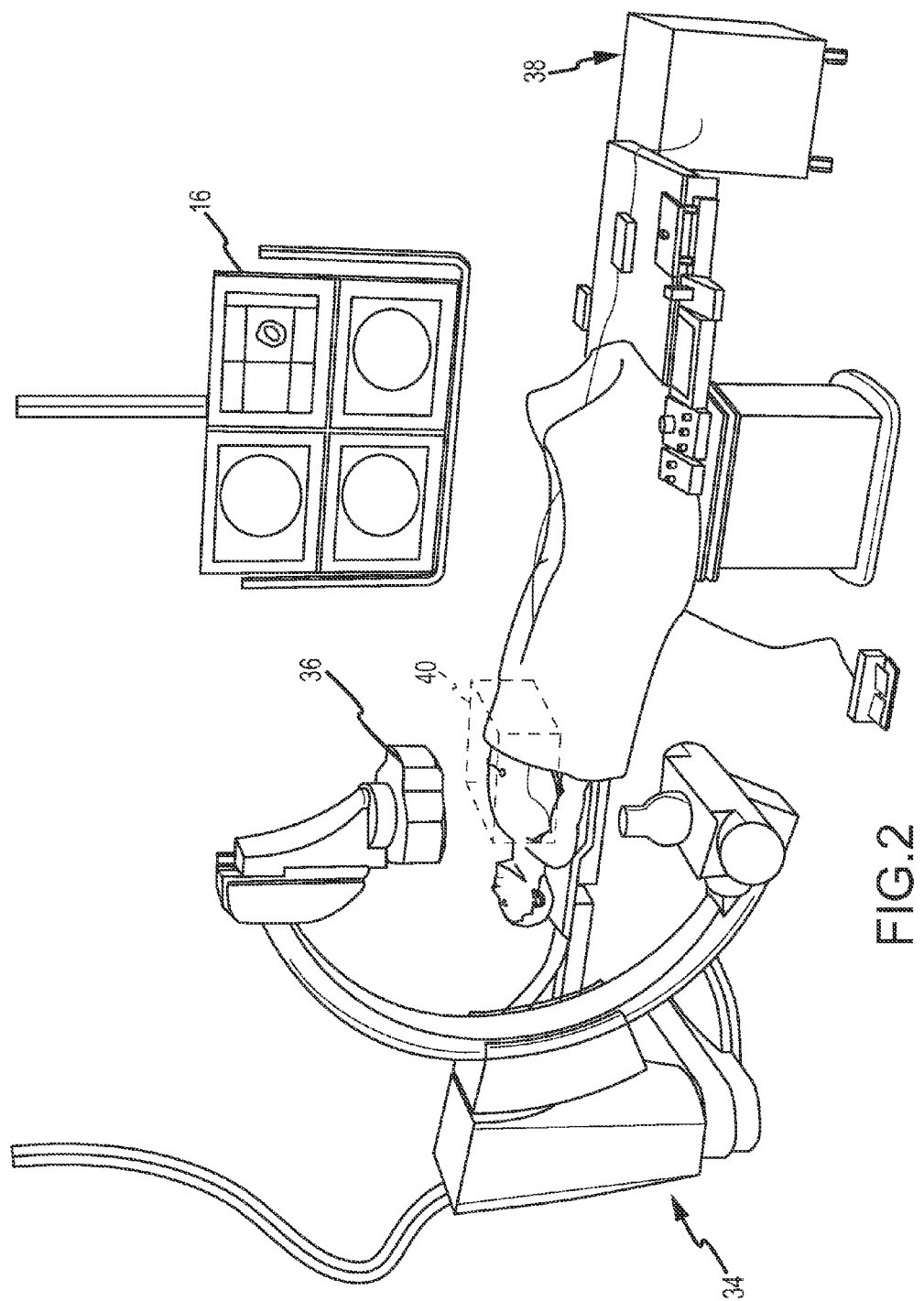
FIG. 2 is a diagrammatic view of the system of FIG. 1 in a catheter-lab environment.

The MPS 20 determines respective locations (i.e., P&O) in the reference coordinate system based on capturing and processing signals received from the magnetic field sensors $24_i$ while such sensors are disposed in a controlled low-strength AC magnetic field (see FIG. 2). Each sensor may comprise one or more magnetic field detection coil(s), and it should be understood that variations as to the number of coils, their geometries, spatial relationships, the existence or absence of cores and the like are possible. From an electromagnetic perspective, these sensors develop a voltage that is induced on the coil residing in a changing magnetic field, as contemplated here. The sensors $24_i$ are thus configured to detect one or more characteristics of the magnetic field(s) in which they are disposed and generate an indicative signal, which is further processed by the MPS 20 to obtain a respective P&O thereof. For one example of a sensor, see U.S. Pat. No. 7,197,354 entitled SYSTEM FOR DETERMINING THE POSITION AND ORIENTATION OF A CATHETER issued to Sobe, hereby incorporated by reference in its entirety.

The first MPS location sensor $24_1$ and optionally (in certain embodiments) the second MPS location sensor $24_2$ are associated with the MPS-enabled medical tool 26. The third MPS sensor, namely, the patient reference sensor (PRS) $24_3$ (if provided in the system 10) is configured to provide a stable, positional reference of the patient's body so as to allow motion compensation for gross patient body movements and/or respiration-induced movements. The PRS $24_3$ may be attached to the patient's manubrium sternum, a stable place on the chest, or other location that is relatively positionally stable. Like the MPS location sensors, the PRS $24_3$ is also configured detect one or more characteristics of the magnetic field in which it is disposed wherein the MPS 20 provides a location reading (e.g., a position and orientation (P&O) reading) indicative of the PRS's three-dimensional position and orientation in the reference coordinate system.

The electro-cardiogram (ECG) monitor 22 is configured to continuously detect an electrical timing signal of the heart organ through the use of a plurality of ECG electrodes (not shown), which may be externally-affixed to the outside of a patient's body. The timing signal generally corresponds to the particular phase of the cardiac cycle, among other things. Generally, the ECG signal(s) may be used by the control unit 12 for ECG synchronized playback of a previously captured sequences of images (cine loop) stored in the database 18. The ECG monitor 22 and ECG-electrodes may both comprise conventional components.

FIG. 2 is a diagrammatic view of the system 10 as incorporated into a larger system that has self-contained imaging capability. It should be understood that while the medical tool shape estimation approach described herein, in certain embodiments, does not require extensive use of fluoroscopy, other aspects of any medical procedure may involve such use, at least intermittently. The system 10 is shown as being incorporated into an fluoroscopic imaging system 34, which may include commercially available fluoroscopic imaging components (i.e., "Catheter Lab"). The MPS 20, in a magnetic field-based embodiment, includes a magnetic transmitter assembly (MTA) 36 and a magnetic processing core 38 for determining location (position and orientation (P&O)) readings. The MTA 36 is configured to generate the magnetic field(s) in and around the patient's chest cavity, in a predefined three-dimensional space identified as a motion box 40. The MPS sensors $24_i$ (where i=1, 2, . . . , n) as described above are configured to sense one or more characteristics of the magnetic field(s) and when the sensors are in the motion box 40, each generate a respective signal that is provided to the magnetic processing core 38. The processing core 38 is responsive to these detected signals and is configured to calculate respective three-dimensional position and orientation (P&O) readings for each MPS sensor $24_i$ in the motion box 40. Thus, the MPS system 20 enables real-time tracking of each sensor $24_i$ in three-dimensional space.

The positional relationship between the image coordinate system and the MPS reference coordinate system may be calculated based on a known optical-magnetic calibration of the system (e.g., established during setup), since the positioning system and imaging system may be considered fixed relative to each other in such an embodiment. However, for other embodiments using other imaging modalities, including embodiments where the image data is acquired at an earlier time and then imported from an external source (e.g., imaging data stored in database 18), a registration step registering the MPS coordinate system and the image coordinate system may need to be performed so that MPS location readings can be properly coordinated with any particular image being used. One exemplary embodiment of an MPS 20 will be described in greater detail below in connection with FIG. 7.

Figure 3:
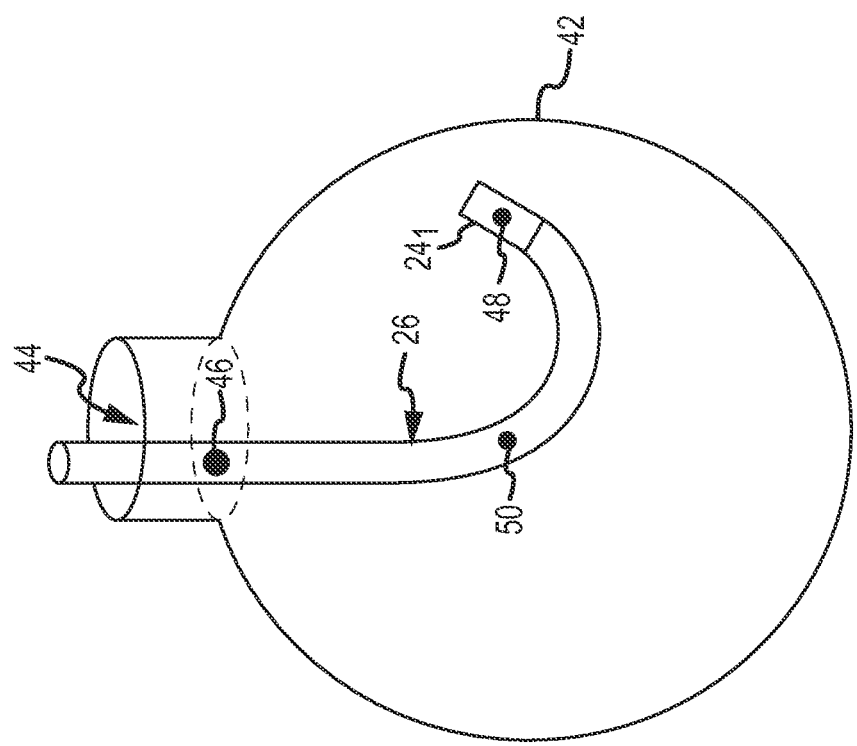
FIG. 3 is a diagrammatic view of a medical tool in a region of interest.

FIG. 3 is a diagrammatic view of a medical tool being inserted in a region of interest in a patient's body. The disclosed method and apparatus overcomes the disadvantages of the prior art by providing a method for reconstructing the curve representing the shape of a tool (e.g., a catheter), fitted with an MPS sensor, during minimal invasive procedures with minimal use of fluoroscopy. According to the disclosed method and apparatus, a tool shape reconstruction is determined using positional constraints and constraints relating to the shape of the tool.

In the illustrative embodiment of FIG. 3, the medical tool takes the form of a catheter 26 having an MPS location sensor $24_1$ at a distal end. The catheter 26 may be maneuvered by a physician towards a desired region of interest 42 (e.g., the right atrium of the heart) contained within the patient's body, which maneuvering involves passing the catheter 26 through an insertion region 44 (i.e., in this example where the destination site is the right atrium, the Superior Vena Cava (SVC) is the insertion region). The illustrated arrangement will be used to demonstrate aspects of positional constraints as used herein. When the catheter 26 enters the right atrium 42, the catheter 26 must first pass through the Superior Vena Cava (SVC) 44. The region proximate the SVC 44 anatomically constrains that portion of the catheter 26 that passes through the SVC 44. Accordingly, one positional constraint, in this example, is the location of the SVC 44, which is designated as location 46. The location of the SVC 44 in the coordinate system may be recorded using the MPS sensor $24_1$ when the catheter 26 passes through the SVC 44. Alternatively, another MPS location sensor (not shown) may be used. Either way, the recorded location defines a so-called positional constraint on the tool shape reconstruction.

Without loss of generality, the above demonstrates one type of positional constraint is the location defined by a point along the tool path where the patient's body anatomically constrains the free movement of the tool in at least one degree of freedom (e.g., location 46). This type of positional constraint exists in this example where the catheter 26 is being inserted through the SVC 44. It should be understood that depending on the medical procedure, the medical tool involved, the range of tool movement contemplated as well other considerations, many other locations may qualify as a constricting type positional constraint. It should be further understood that a degree of freedom may correspond to any one or more of the axes or orientation angles in the reference coordinate system. In the example, the SVC 44 constrains the range of lateral movement of the catheter but not axial (up/down) movement of the catheter. This is true at the moment the catheter is first inserted through the SVC 44 and remains true even at later time as advancement of the catheter proceeds into the right atrium.

An additional type of positional constraint may be the location of the MPS sensor $24_1$ at the tip of the catheter 26 at a time when the tool shape reconstruction is calculated (i.e., the current tool location). An example of this type of positional constraint is shown as location 48. This positional constraint is relevant to the tool shape reconstruction at the current time. What ties the relevancy of the earlier recorded location (i.e., location 46) to the current tool shape reconstruction is the anatomical constraint imposed by the patient's body on the subsequent motion of the tool. It should be understood that the path of the tool's tip (i.e., where the location sensor is embedded in the illustrative embodiment) does not necessarily resemble its current shape. Therefore, it makes sense to only use points along the tool path as positional constraints where the tool is more strictly bounded by the patient's anatomy per se. For example, the history of the positions of the catheter tip freely wandering in the right atrium cannot serve as a basis to reconstruct its current shape.

With continued reference to FIG. 3, the control unit 12 is configured to determine the location 46 through interaction with a user. The user may visually detect (e.g., according to an inspection of an x-ray image of the region of interest 42) when the catheter 26 passes through the SVC 44, and more particularly when a part of the catheter (e.g., the tip) passes through the SVC 44 (i.e., the anatomically constraining location in the body). The control unit 12 may superimpose a representation of the catheter tip's location on the x-ray image being displayed, for example, in the form of crosshairs or the like, to facilitate user recognition of when the tool is in the desired location to record an MPS location reading. The control unit 12 includes a user interface (e.g., a graphical user interface (GUI)) configured to receive an input signal from the user to record the MPS location reading when this condition has been detected visually. The signal may take the form of some user-initiated action such as actuation of a joystick, a push button, a pointing device (e.g., mouse, stylus and digital tablet, track-ball, touch pad) or by any other conventional means. The user interface of the control unit 12 recognizes the user request and the control unit 12 then records the MPS location reading corresponding to the location 46 (i.e., as detected by the MPS sensor $24_1$).

In addition, the estimation block 28 is configured to utilize other external inputs, such as the location of a landmark representing an anatomical constriction on tool movement. A constrictive landmark is similar to what has been described above for location 46. The control unit 12 may provide a mechanism for defining such a landmark (virtual landmark), which may in turn be used by the estimation block 28 to compute the tool shape reconstruction. One approach for defining a virtual landmark may be as seen by reference to U.S. Patent Publication 2006/0058647, application Ser. No. 11/233,420 entitled "METHOD AND SYSTEM FOR DELIVERING A MEDICAL DEVICE TO A SELECTED POSITION WITHIN A LUMEN", to Strommer, hereby incorporated by reference in its entirety. The control unit 12 may be configured to employ the general steps of (i) placing a MPS-enabled device at the desired landmark, by means of visualization on either live or pre-recorded image; and (ii) using a graphical user interface (GUI) or other control to designate the landmark at the location of the tip of the MPS-enabled device. The estimation block 28 may use the location (P&O) of the constrictive landmark in the tool shape estimation.

According to another embodiment, the estimation block 28 uses the locations 46, 48 in conjunction with at least one further location, such as the location 50 obtained through the use of at least one further MPS location sensor (not shown) mounted on the catheter 26 at a point intermediate its distal and proximal ends. The locations 46, 48, 50 collectively define a set of positional constraints used by the estimation block 28 in determining the catheter's current shape.

As described above, the estimation block 28 also receives a shape constraint as an input (input block $30_1$) for use in its processing logic to reconstruct the tool's current shape. The shape constraint corresponds to the tool's relaxation shape. In one embodiment, the relaxation shape is predetermined and defined by a model stored in memory (not shown) accessible to the estimation block 28. The model may reflect a mathematical description of the curve (e.g., in the form of a polynomial expression) that corresponds to the relaxation shape of the catheter 26. For example only, for a fixed shaped catheter whose relaxation shape is defined in a Y-Z coordinate plane, such a relaxation shape model may define a Z-axis value for a given Y-axis value using, for example, a polynomial expression like $z=ay^2+by+c$ where a, b and c are coefficients (i.e., this assumes a second order polynomial—of course, higher order polynomial expressions are possible as are other models employing different mathematical descriptions). It should be understood that the relaxation shape may be described in three-dimensions as well and that the above-description referenced to a 2D mathematical description is exemplary only and not limiting in nature.

In another embodiment, the model may alternatively be configured to accommodate non-fixed shape tools, such as, for example, a steerable catheter. In such an alternate embodiment, however, the model may be configured to require the input of additional pieces of information, such as the location(s) of one or more restricting landmark(s) in close proximity to the tool tip and/or one or more location(s) from one or more additional MPS location sensors fitted to the non-fixed shape tool.

In another embodiment, the model may in addition receive mechanical characteristics of the tool as an input. These characteristics may be expressed as position-dependent functions of mechanical admittance to force, i.e., for each point along the tool, what geometrical displacement from the relaxation shape will result from exerting a force unit. This function may be expressed as a series of step-wise functions or as higher dimension polynomials expressing continuous functions of force admittance as functions of the location along the tool.

Figure 4:
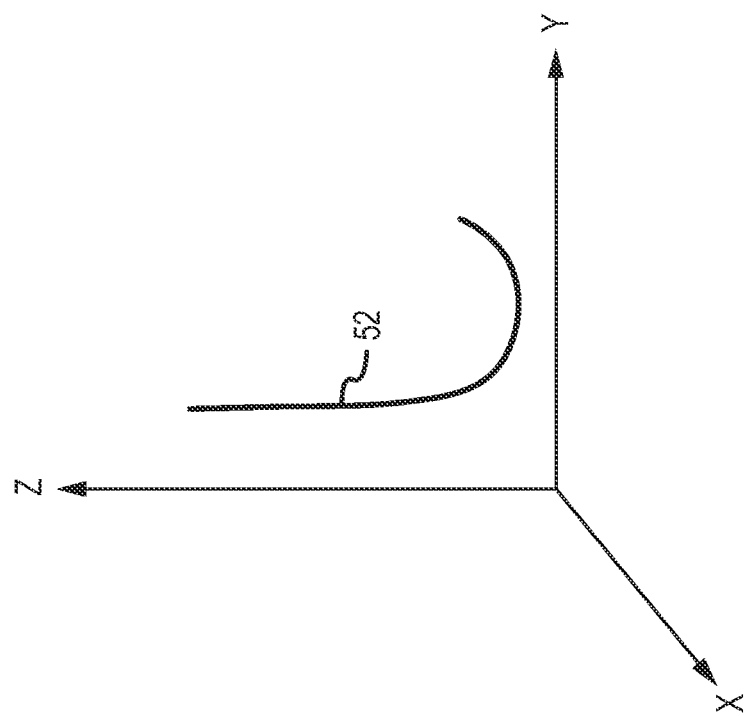
FIG. 4 is a diagrammatic view of a curve representing the shape of the tool.

FIG. 4 is a diagrammatic view of a curve (i.e., the tool shape reconstruction) produced by the estimation block 28 representing the shape of the medical tool, such as the catheter 26 in FIG. 3. The reconstruction 52, in the depiction, may be, for example, a spline representation of the curve. A spline is a functional representation of a curve. Any curve may be approximated by a function or a set of functions. Thus the reconstruction 52 may include one or more functions in order to fully describe the curve. The estimation block 28 produces the reconstruction 52 by processing the input information from the shape constraint input block $30_1$ and the positional constraints input block $30_2$ and converging upon a solution consistent with the positional and shape constraints. One way of computing the optimal tool shape given the constraints is to perform an iterative search of a global minimum over a cost function associated with the relaxation shape of the tool. An example of a straight-forward cost function is the symmetric area between the current iteration's computed shape and the relaxation shape of the tool. The iteration step will try to reduce the value of the cost function in the next iteration by moving a part of the next iteration's computed shape closer to the relaxation shape. It should be noted that the constraints to be met in this computation may have different priorities: the portion (or portions) of the tool where MPS sensors are equipped can hardly be altered, as the position and orientation of the sensor is very accurate; whereas the relation between the portion (or portions) of the tool and other constraints, like landmarks, may not be as rigid (i.e., such landmarks do not necessarily indicate the exact location through which the tool currently passes). Moreover, while a sensor position and orientation is rigidly tied to a specific point along the tool (e.g., the tool's tip), it is not known exactly which part of the tool resides at a constraint like a landmark. The algorithm uses this prioritization of constraints to iteratively search for a minimum cost function value. The reconstruction 52 produced by the estimation block 28 represents the current shape of the tool.

Once the estimation block 28 has produced the above-described reconstruction 52 of the tool's shape, one of the main uses for the reconstruction is to be superimposed on a previously acquired image using the super-imposing processor 32. First, the reconstruction of the tool's shape must be located in the reference coordinate system (i.e., the MPS coordinate system). This may be achieved by the control unit 12 through the use of one of MPS location readings indicative of the tool's current location obtained from MPS 20 in conjunction with the tool shape reconstruction. The control unit 12 may determine the location after the shape determination or as a unitary process with the tool shape calculation. In addition, the image coordinate system must be registered with the reference coordinate system (described above).

The display of the tool, for example, as a 3D object projected onto a previously-acquired image enables the operator to perform the clinical routine (i.e., navigation) without using live fluoroscopy. For example, cannulation of the coronary sinus (CS) can be done with a 3D catheter shape displayed over a recorded cine-loop (i.e., onto each frame in the series of frames) without the use of fluoroscopy.

The superimposing processor 32 includes the capability of projecting the 3D representation of the tool's shape and location (once determined) on a previously recorded 2D image of the region of interest or in the case of cine-loops (CL), onto each 2D image in the CL sequence. The projection may be graphically superimposed onto the image to form a composite image, which is displayed. The superimposing processor 32 may comprise components and approaches known in the art, for example, as seen by reference to U.S. Pat. Pub. 2006/0058647, application Ser. No. 11/233,420 entitled METHOD AND SYSTEM FOR DELIVERING A MEDICAL DEVICE TO A SELECTED POSITION WITHIN A LUMEN, to Strommer et al., hereby incorporated by reference in its entirety. As described, once the reference coordinate system and the image (e.g., x-ray imaging) coordinate systems are co-registered, as described above, the 3D coordinates of the tool reflecting its shape and location may be multiplied by a coordinate transformation matrix that computes the corresponding 2D coordinates on the displayed image. This approach is exemplary only and not limiting in nature.

Additionally, the control unit 12 may be configured to include a respiration compensation algorithm (not shown) configured to learn the motion induced by the patient's respiration, based on location (P&O) readings from the PRS $24_3$. Thus, with the availability of the ECG signal and a PRS signal, the control unit 12 can replay a cine loop in an ECG synchronized and respiration-compensated manner, with the tool shape reconstruction (curve) superimposed thereon. Through the foregoing, previously acquired imaging of the region of interest can be displayed with a superimposed, accurate representation of the medical tool's shape and location, without extensive or even additional use of fluoroscopy, thereby reducing patient exposure to x-rays.

Figure 5:
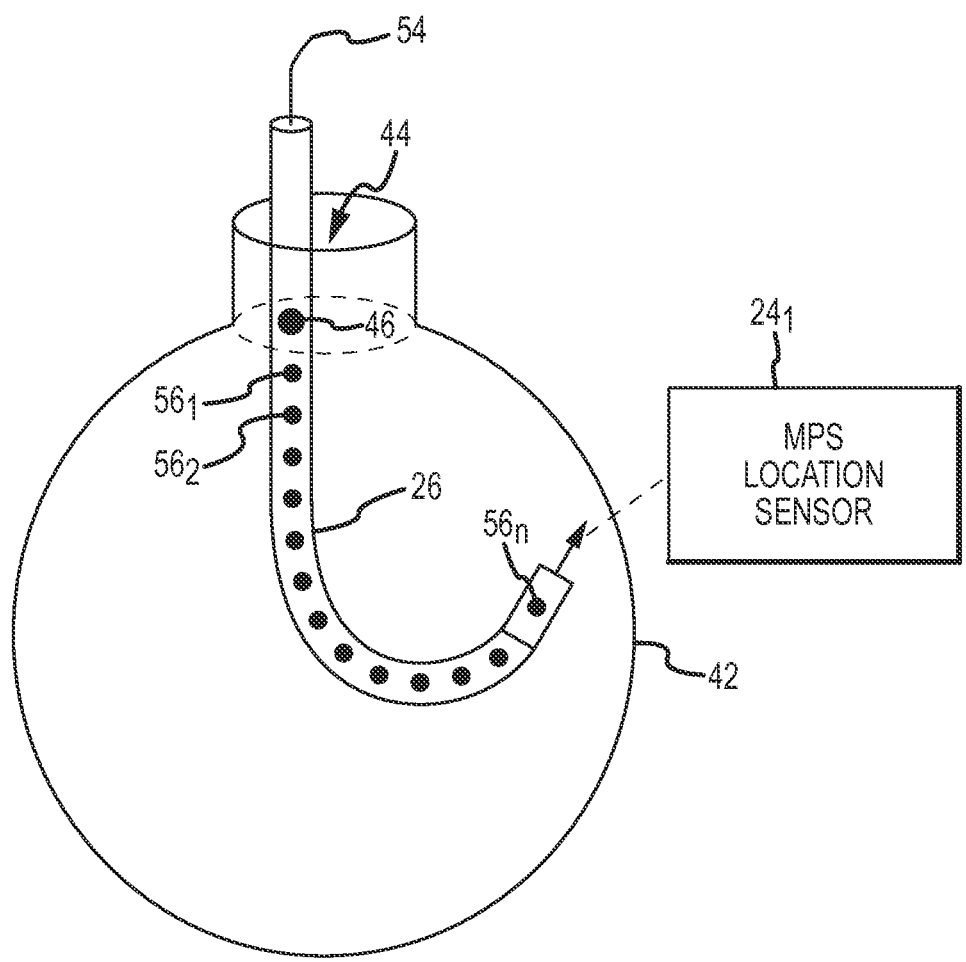
FIG. 5 is a diagrammatic view of a medical tool fitted with a centrally-disposed guidewire, in an alternate embodiment.

FIG. 5 is a diagrammatic view of a region of interest illustrating a further embodiment where the medical tool is a catheter having a centrally-deployed guidewire 54. In a first variation, a positional constraint, namely, the intermediate (mid-tool) location 50 (see FIG. 3) may alternatively be obtained using a guidewire-mounted MPS location sensor. As before, the estimation block 28 is configured to use the location 50 along with the other locations 46 and 48 as positional constraints in producing a reconstruction of the catheter's shape.

In a second variation, a plurality of MPS location readings obtained using a guidewire-mounted MPS location sensor $24_1$ (e.g., mounted at its distal end) are recorded as the guidewire 54 passes through the catheter 26. In the illustrative embodiment, the catheter 26 is kept stable while the guidewire 56 moves therethrough, effecting a relative movement between the stable catheter, on the one hand, and the moving guidewire on the other. For movement, the guidewire 54 may be advanced or withdrawn. While the guidewire 54 is moving, the MPS 20 provides a series of MPS location readings $56_1, 56_2, \ldots 56_n$ indicative of the respective locations (i.e., position and orientation) taken by the tip of the guidewire 54 (i.e., the tip being where the sensor is attached) along a guidewire path. The series of location readings $56_1, 56_2, \ldots, 56_n$ are recorded.

Since usually there is not much slack for the guidewire inside the guidewire lumen, the guidewire 54 and the catheter 26 may be considered close to concentric. Accordingly, the guidewire path fairly approximates the catheter shape. The estimation block 28 is configured to use the readings $56_i$ (where i=1 to n) to compute a 3D representation of the relaxation shape of the catheter 26. Note, that the tool does not necessarily need to be at the desired destination site in the region of interest in the patient's body before the series of location readings $56_i$ are acquired, since the relaxation shape is what is being determined by the estimation block 28. In an alternative embodiment, however, the series of MPS location readings $56_i$ are acquired after the tool has reached the desired destination site, in which case the MPS location readings $56_i$ expressed in the reference coordinate system, not only can be used to derive the tool's relaxation shape, but can also be used to provide information as to the location of the tool in the reference coordinate system.

Figure 6:
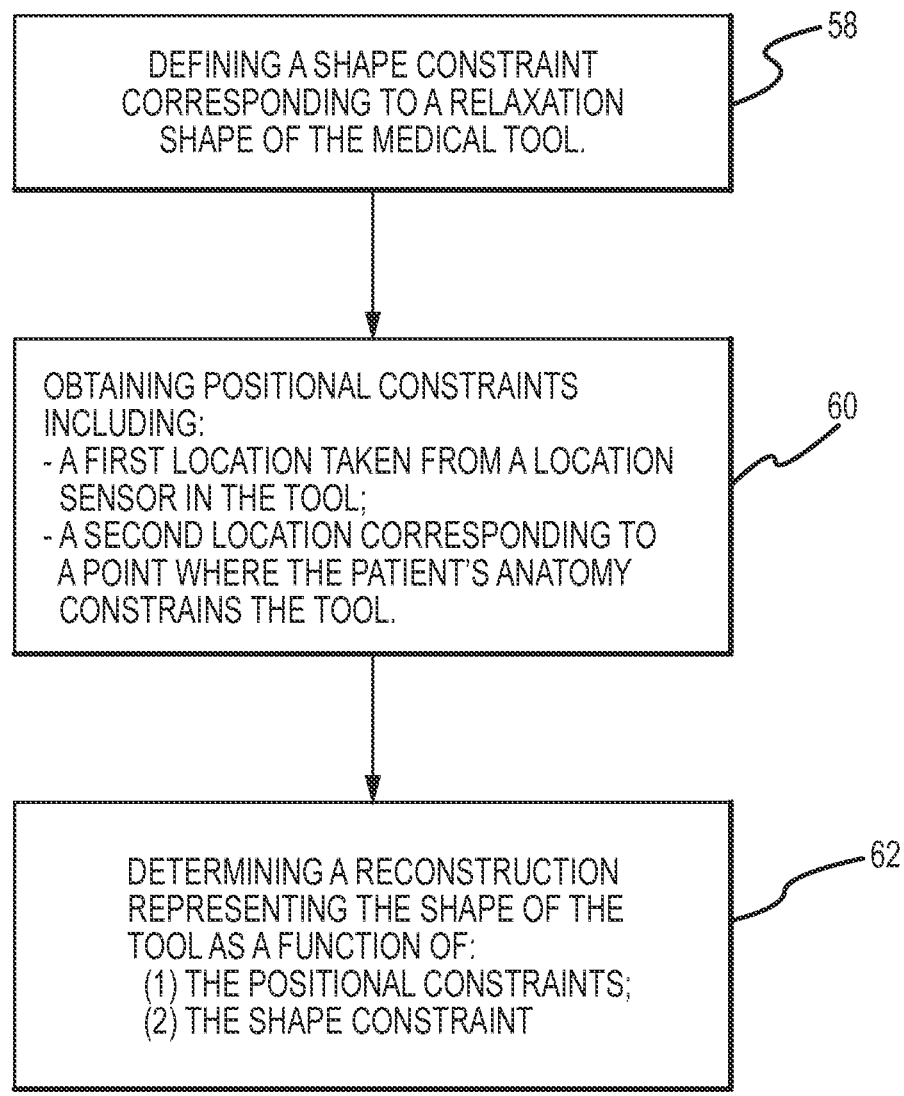
FIG. 6 is a flowchart showing a method for tool shape reconstruction.

FIG. 6 is a flowchart of a method of reconstructing (estimating) the shape of a medical tool. The method begins in step 58.

In step 58, the shape constraint block $30_1$ provides a tool shape constraint (i.e., the tool's relaxation shape) to the estimation block 28. As described above, the tool's relaxation shape may be predetermined and stored in a model for use by the estimation block 28, or alternatively the relaxation shape may be determined during use through the collection of MPS location readings $56_i$ using a guidewire fitted with an MPS location sensor.

In step 60, the positional constraint block $30_2$ provides one or more positional constraints to the estimation block 28. The positional constraints may take the form of locations (e.g., 3D coordinates) defined in the reference coordinate system. As described above, one type of positional constraint may be a location defined by a point along a tool path where the patient's anatomy constrain the free tool movement of the tool in at least one degree of freedom. Another type of positional constraint may be one or more current locations at one or more different points on the tool once the tool has been positioned at a desired destination site. In addition, locations of anatomically constricting landmarks, as described above, may also be used.

In step 62, the estimation block 28 calculates a reconstruction representing the tool's shape as a function of: (1) the shape constraint from step 58 and (2) the one or more positional constraints from step 60. After the estimation block 28 generates the reconstruction of the tool's shape, the reconstruction (e.g., defined in three-dimensions, in an embodiment) may be thereafter used for a variety of purposes. For example, the superimposing processor 32 may graphically superimpose a projection of the reconstruction onto a previously acquired image of the region of interest.

While the above described use involves displaying the tool as a 3D object superimposed on a previously-acquired image, variations are possible. For example, variations may include superimposing the reconstructed tool onto imaging acquired using another imaging modality registered with the MPS 20, such as either two-dimensional (2D) imaging modalities (e.g., echo-based imaging) or three-dimensional (3D) imaging modalities (e.g., computed tomography (CT) or rotational angiography). Another variation may involve using the estimated tool shape apart from its specific location. For example, the estimated shape alone may be used in a process for detecting potential tool dislodgement (and for generating a warning) when the computed tool's shape varies from its relaxation shape by more than a predetermined amount, indicative of a situation where the tool has experienced an excessive force. In such a situation, detecting tool dislodgement (or impending tool dislodgement) may involve determining when the value of the resulting cost function associated with the computed shape is larger than a pre-defined threshold. U.S. application Ser. No. 12/651,148 filed 31 Dec. 2009 entitled "PROLAPSE DETECTION AND TOOL DISLODGEMENT DETECTION" owned by the common assignee of the present invention, is hereby incorporated by reference in its entirety. The process of tool dislodgement using the tool's estimated shape, as described above, may be used in connection with the tool dislodgement system of U.S. Ser. No. 12/651,148.

Figure 7:
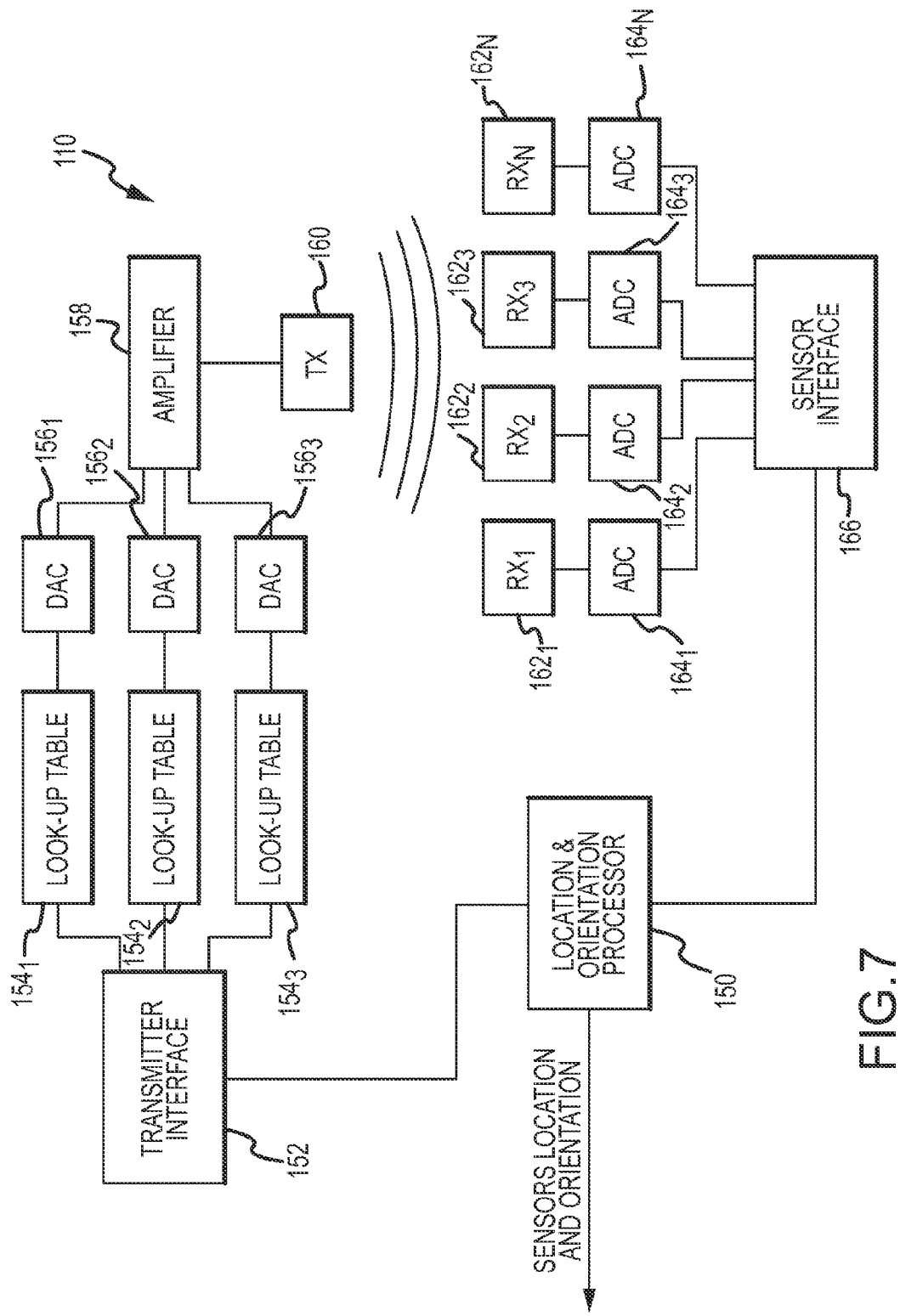
FIG. 7 is a schematic and block diagram view of one exemplary embodiment of a medical positioning system (MPS) as shown in block form in FIG. 1.

FIG. 7 is a schematic and block diagram of one exemplary embodiment of MPS 20, designated as an MPS 108, as also seen by reference to U.S. Pat. No. 7,386,339, referred to above, and portions of which are reproduced below, which generally describes, at least in part, the gMPS™ medical positioning system commercially offered by MediGuide Ltd. It should be understood that variations are possible, for example, as also seen by reference to U.S. Pat. No. 6,233,476 entitled MEDICAL POSITIONING SYSTEM, also hereby incorporated by reference in its entirety. Another exemplary magnetic field-based MPS is the Carto™ system commercially available from Biosense Webster, and as generally shown and described in, for example, U.S. Pat. No. 6,498,944 entitled "Intrabody Measurement," and U.S. Pat. No. 6,788,967 entitled "Medical Diagnosis, Treatment and Imaging Systems," both of which are incorporated herein by reference in their entireties. Accordingly, the following description is exemplary only and not limiting in nature.

MPS system 110 includes a location and orientation processor 150, a transmitter interface 152, a plurality of look-up table units $154_1$, $154_2$ and $154_3$, a plurality of digital to analog converters (DAC) $156_1$, $156_2$ and $156_3$, an amplifier 158, a transmitter 160, a plurality of MPS sensors $162_1$, $162_2$, $162_3$ and $162_N$, a plurality of analog to digital converters (ADC) $164_1$, $164_2$, $164_3$ and $164_N$ and a sensor interface 166.

Transmitter interface 152 is connected to location and orientation processor 150 and to look-up table units $154_1$, $154_2$ and $154_3$. DAC units $156_1$, $156_2$ and $156_3$ are connected to a respective one of look-up table units $154_1$, $154_2$ and $154_3$ and to amplifier 158. Amplifier 158 is further connected to transmitter 160. Transmitter 160 is also marked TX. MPS sensors $162_1$, $162_2$, $162_3$ and $162_N$ are further marked $RX_1$, $RX_2$, $RX_3$ and $RX_N$, respectively. Analog to digital converters (ADC) $164_1$, $164_2$, $164_3$ and $164_N$ are respectively connected to sensors $162_1$, $162_2$, $162_3$ and $162_N$ and to sensor interface 166. Sensor interface 166 is further connected to location and orientation processor 150.

Each of look-up table units $154_1$, $154_2$ and $154_3$ produces a cyclic sequence of numbers and provides it to the respective DAC unit $156_1$, $156_2$ and $156_3$, which in turn translates it to a respective analog signal. Each of the analog signals is respective of a different spatial axis. In the present example, look-up table $154_1$ and DAC unit $156_1$ produce a signal for the X axis, look-up table $154_2$ and DAC unit $156_2$ produce a signal for the Y axis and look-up table $154_3$ and DAC unit $156_3$ produce a signal for the Z axis.

DAC units $156_1$, $156_2$ and $156_3$ provide their respective analog signals to amplifier 158, which amplifies and provides the amplified signals to transmitter 160. Transmitter 160 provides a multiple axis electromagnetic field, which can be detected by MPS sensors $162_1$, $162_2$, $162_3$ and $162_N$. Each of MPS sensors $162_1$, $162_2$, $162_3$ and $162_N$ detects an electromagnetic field, produces a respective electrical analog signal and provides it to the respective ADC unit $164_1$, $164_2$, $164_3$ and $164_N$ connected thereto. Each of the ADC units $164_1$, $164_2$, $164_3$ and $164_N$ digitizes the analog signal fed thereto, converts it to a sequence of numbers and provides it to sensor interface 166, which in turn provides it to location and orientation processor 150. Location and orientation processor 150 analyzes the received sequences of numbers, thereby determining the location and orientation of each of the MPS sensors $162_1$, $162_2$, $162_3$ and $162_N$. Location and orientation processor 150 further determines distortion events and updates look-up tables $154_1$, $154_2$ and $154_3$, accordingly.

It should be understood that the system 10, particularly control unit 12, as described above may include conventional processing apparatus known in the art (i.e., both hardware and/or software), including the capability of executing pre-programmed instructions stored in an associated memory, all performing in accordance with the functionality described herein. It is contemplated that the methods described herein, including without limitation the method steps of embodiments of the invention, may be programmed in a preferred embodiment, with the resulting software being stored in an associated memory and may also constitute the means for performing such methods. Implementation of embodiments, in software, in view of the foregoing enabling description, would require no more than routine application of programming skills by one of ordinary skill in the art. The system may further be of the type having both ROM, RAM, a combination of non-volatile and volatile (modifiable) memory so that the software can be stored and yet allow storage and processing of dynamically produced data and/or signals.

Although numerous embodiments of this invention have been described above with a certain degree of particularity, those skilled in the art could make numerous alterations to the disclosed embodiments without departing from the spirit or scope of this invention. All directional references (e.g., plus, minus, upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. An apparatus for determining a shape of a medical tool in a region of interest in a patient's body, comprising:
a medical positioning system configured to produce location readings with respect to points within said region of interest in accordance with an output of a location sensor connected to said tool moving within said region of interest, each location reading being associated with a three-dimensional reference coordinate system; and
a control unit including a main processor and an associated memory wherein said control unit is coupled to said medical positioning system, said control unit being configured to execute pre-programmed instructions stored in said associated memory to determine a reconstruction representing the shape of said tool as a function of (1) a positional constraint that includes a first location corresponding to a first location reading produced by the medical positioning system, said first location reading indicating a constricting point along a tool path where said patient's body anatomically constrains movement of said tool in at least one degree of freedom, and (2) a shape constraint corresponding to a relaxation shape of said tool, wherein said control unit is configured through a user interface to receive an input from a user to record said first location reading produced by said medical positioning system, and wherein said signal to record said first location reading is received at a time when the medical tool is constrained by said patient's body.

2. The apparatus of claim 1 further including a superimposing processor configured to graphically superimpose said reconstruction on an image of said region of interest acquired at an earlier time.

3. The apparatus of claim 1 wherein said reconstruction representing the shape of the tool comprises a function or a plurality of functions.

4. The apparatus of claim 1 wherein said reconstruction representing the shape of the tool comprises a spline.

5. The apparatus of claim 1 wherein said positional constraint further includes a second location in said coordinate system corresponding to a second location reading, said second location indicating the current location of said tool in said region of interest.

6. The apparatus of claim 5 wherein said location sensor in said tool is a first location sensor, said tool further including a second location sensor wherein said positional constraint further includes a third location corresponding to a third location reading, said third location indicating the location of said second location sensor.

7. The apparatus of claim 6 wherein at least one of said first, second and third locations comprise a respective position and orientation in said coordinate system.

8. The apparatus of claim 1 wherein said relaxation shape is determined in accordance with a model, said model approximating the relaxation shape of said tool in three-dimensional space.

9. The apparatus of claim 8 wherein said model comprises a polynomial expression.

10. The apparatus of claim 8 wherein said tool includes a centrally-disposed guidewire having a guidewire location sensor affixed at a distal end thereof, said medical positioning system being configured to produce a plurality of location readings indicative of the respective locations of said guidewire sensor while said guidewire moves in said catheter, said control unit being configured to execute pre-programmed instructions stored in said associated memory to model said relaxation shape based on said plurality of recorded location readings.

11. The apparatus of claim 1 wherein said control unit includes a tool shape estimation means for determining said reconstruction representing said tool shape wherein said tool shape estimation means includes said processor configured to execute pre-programmed instructions stored in said associated memory for determining said reconstruction representing said tool shape.

12. A method for determining a shape of a medical tool within a region of interest in a patient's body, comprising:
(A) defining, using a computer processing apparatus, a shape constraint corresponding to a tool relaxation shape;
(B) defining a positional constraint that includes acquiring a first location of a first location sensor of the tool by using a medical positioning system, the first location indicating a constricting point along a tool path where the patient's body anatomically constrains movement of the tool in at least one degree of freedom; and
(C) determining, using the computer processing apparatus, a reconstruction representing the shape of the tool as a function of the shape constraint and the positional constraint.

13. The method of claim 12 further including:
superimposing, using a superimposing processor, the reconstruction of the tool's shape on an image of the region of interest acquired at an earlier time.

14. The method of claim 12 wherein determining the reconstruction includes representing, using the computer processor apparatus, the shape of the tool as a spline.

15. The method of claim 12 wherein the first location is associated with a coordinate system, and wherein defining the positional constraint includes:
determining a second location in the coordinate system using the medical positioning system, the second location indicating the current location of the tool in the region of interest.

16. The method of claim 15 wherein defining the positional constraint includes:
determining a third location in the coordinate system using a second location sensor of the tool wherein the second location sensor is displaced from the first location sensor of the tool.

17. The method of claim 16 wherein at least one of said first, second and third locations comprise a respective position and orientation in said coordinate system.

18. The method of claim 12 wherein the tool includes a lumen configured for carrying a guidewire therethrough wherein the guidewire has a guidewire sensor affixed at a distal end thereof, said defining a relaxation shape includes:
maneuvering the tool to a desired site in the patient's body;
confirming that the tool is stable;
moving the guidewire within the tool;
while performing said moving, recording a plurality of location readings indicative of respective locations of the guidewire location sensor; and
determining the relaxation shape based on the plurality of recorded location readings.

19. An apparatus for determining a shape of a medical tool in a region of interest in a patient's body, comprising:
a medical positioning system configured to produce location readings with respect to points within said region of interest in accordance with an output of a location sensor connected to said tool moving within said region of interest, each location reading being associated with a three-dimensional reference coordinate system; and a control unit including a main processor and an associated memory wherein said control unit is coupled to said medical positioning system, said control unit being configured to execute pre-programmed instructions stored in said associated memory to determine a reconstruction representing the shape of said tool as a function of (1) a positional constraint that includes a first location corresponding to a first location reading produced by the medical positioning system, said first location reading indicating a constricting point along a tool path where said patient's body anatomically constrains movement of said tool in at least one degree of freedom, and (2) a shape constraint corresponding to a relaxation shape of said tool, wherein said relaxation shape is determined in accordance with a model, said model approximating the relaxation shape of said tool in three-dimensional space.

* * * * *